United States Patent
Lehman et al.

(10) Patent No.: US 8,067,399 B2
(45) Date of Patent: Nov. 29, 2011

(54) METHOD AND APPARATUS FOR TRANSDERMAL OR TRANSMUCOSAL APPLICATION OF TESTOSTERONE

(75) Inventors: Leah M. Lehman, Green Oaks, IL (US); Stephen M. Simes, Long Grove, IL (US)

(73) Assignee: Antares Pharma IPL AG, Zug (CH)

( * ) Notice: Subject to any disclaimer, the term of this patent is extended or adjusted under 35 U.S.C. 154(b) by 951 days.

(21) Appl. No.: 11/441,311

(22) Filed: May 24, 2006

(65) Prior Publication Data

US 2006/0270642 A1 Nov. 30, 2006

Related U.S. Application Data

(60) Provisional application No. 60/685,132, filed on May 27, 2005.

(51) Int. Cl.
*A61K 31/56* (2006.01)
(52) U.S. Cl. ........................................ 514/170; 514/182
(58) Field of Classification Search .................. 514/170, 514/182
See application file for complete search history.

(56) References Cited

U.S. PATENT DOCUMENTS

| | | | | |
|---|---|---|---|---|
| 2,990,332 A | 6/1961 | Keating | ............................ | 167/65 |
| 3,143,465 A | 8/1964 | Keating | ............................ | 167/65 |
| 3,891,696 A | 6/1975 | Bodor et al. | ..................... | 560/142 |
| 3,989,816 A | 11/1976 | Rajadhyaksha | ................. | 424/60 |
| 4,082,881 A | 4/1978 | Chen et al. | ..................... | 424/241 |
| 4,221,778 A | 9/1980 | Raghunathan | ................... | 424/31 |
| 4,315,925 A | 2/1982 | Hussaiin et al. | ............... | 424/239 |
| 4,316,893 A | 2/1982 | Rajadhyaksha | ................. | 424/180 |
| 4,383,993 A | 5/1983 | Hussaiin et al. | ............... | 424/239 |
| 4,390,532 A | 6/1983 | Stuttgen et al. | ................ | 424/240 |
| 4,405,616 A | 9/1983 | Rajadhyaksha | ................. | 424/60 |
| 4,537,776 A | 8/1985 | Cooper | ........................... | 514/424 |
| 4,557,934 A | 12/1985 | Cooper | ........................... | 424/128 |
| 4,568,343 A | 2/1986 | Leeper et al. | ................... | 604/896 |
| 4,597,961 A | 7/1986 | Etscorn | .......................... | 424/448 |
| 4,704,406 A | 11/1987 | Stanislaus et al. | ............. | 514/570 |
| 4,764,381 A | 8/1988 | Bodor et al. | .................... | 424/449 |
| 4,783,450 A | 11/1988 | Fawzi et al. | ..................... | 514/78 |
| 4,808,411 A | 2/1989 | Lu et al. | ........................... | 424/441 |
| 4,832,953 A | 5/1989 | Campbell et al. | .............. | 424/448 |
| 4,863,970 A | 9/1989 | Patel et al. | ...................... | 514/784 |
| 4,883,660 A | 11/1989 | Blackman et al. | ............... | 424/78 |
| 4,952,560 A | 8/1990 | Kigasawa et al. | ................. | 514/2 |
| 4,956,171 A | 9/1990 | Chang | ............................. | 424/449 |

(Continued)

FOREIGN PATENT DOCUMENTS

EP  0 249 397 A2  12/1987

(Continued)

OTHER PUBLICATIONS

W. H. Catherino et al., "Nomegestrol Acetate, a Clinically Useful 19-Norprogesterone Derivative which Lacks Estrogenic Activity," J. Steroid Biochem. Molec. Biol. vol. 55(2):239-246 (1995).

(Continued)

*Primary Examiner* — San-Ming Hui
(74) *Attorney, Agent, or Firm* — Winston & Strawn LLP

(57) ABSTRACT

Methods, formulations, and devices for providing transdermal or transmucosal delivery of active agents to subjects in need thereof. The formulations and methods treat symptoms of hormonal disorders including hypogonadism, female sexual desire disorder, female menopausal disorder, and adrenal insufficiency.

13 Claims, 3 Drawing Sheets

Mean Change from Baseline in 4-Week Sexual Event Rate

U.S. PATENT DOCUMENTS

| | | | |
|---|---|---|---|
| 4,973,468 A | 11/1990 | Chiang et al. | 424/449 |
| 5,041,439 A | 8/1991 | Kasting et al. | 514/227.2 |
| 5,053,227 A | 10/1991 | Chiang et al. | 424/448 |
| 5,059,426 A | 10/1991 | Chiang et al. | 424/449 |
| 5,064,654 A | 11/1991 | Berner et al. | 424/448 |
| 5,071,657 A | 12/1991 | Oloff | 424/486 |
| 5,112,842 A | 5/1992 | Zierenberg et al. | 514/367 |
| 5,128,138 A | 7/1992 | Blank | 424/449 |
| 5,134,127 A | 7/1992 | Stella et al. | 514/58 |
| 5,164,190 A | 11/1992 | Patel et al. | 424/448 |
| 5,175,190 A | 12/1992 | Burton et al. | 514/560 |
| 5,178,879 A | 1/1993 | Adekunle et al. | 424/484 |
| 5,188,825 A | 2/1993 | Hes et al. | 424/78.1 |
| 5,225,189 A | 7/1993 | Pena | 424/70 |
| 5,230,896 A | 7/1993 | Yeh et al. | 424/443 |
| 5,232,703 A | 8/1993 | Blank | 424/449 |
| 5,238,933 A | 8/1993 | Catz | 514/236.2 |
| 5,278,176 A | 1/1994 | Lin | 514/343 |
| 5,352,457 A | 10/1994 | Jenkins | 424/448 |
| 5,371,005 A | 12/1994 | Fujishiro et al. | 435/190 |
| 5,374,421 A | 12/1994 | Tashiro et al. | 424/70.12 |
| 5,376,645 A | 12/1994 | Stella et al. | 514/58 |
| 5,380,763 A | 1/1995 | Sato et al. | 514/724 |
| 5,397,771 A | 3/1995 | Bechgaard et al. | 514/2 |
| 5,453,279 A | 9/1995 | Lee et al. | 424/448 |
| 5,527,832 A | 6/1996 | Chi et al. | 514/772.4 |
| 5,532,278 A | 7/1996 | Aberg et al. | 514/617 |
| 5,549,888 A | 8/1996 | Venkateswaran | 424/78.02 |
| 5,552,153 A | 9/1996 | Behl | 424/449 |
| 5,576,279 A | 11/1996 | Pyles | 510/122 |
| 5,580,574 A | 12/1996 | Behl et al. | 424/449 |
| 5,601,839 A | 2/1997 | Quan et al. | 424/448 |
| 5,602,017 A | 2/1997 | Fujishiro et al. | 435/190 |
| 5,603,947 A | 2/1997 | Wong et al. | 424/448 |
| 5,629,021 A | 5/1997 | Wright | 424/489 |
| 5,633,008 A | 5/1997 | Osborne et al. | 424/448 |
| 5,658,587 A | 8/1997 | Santus et al. | 424/448 |
| 5,660,839 A | 8/1997 | Allec et al. | 424/401 |
| 5,662,890 A | 9/1997 | Punto et al. | 424/59 |
| 5,665,560 A | 9/1997 | Fujishiro et al. | 435/11 |
| 5,677,346 A | 10/1997 | Aberg et al. | 51/617 |
| 5,716,638 A | 2/1998 | Touitou | 424/450 |
| 5,719,197 A | 2/1998 | Kanios et al. | 514/772.6 |
| 5,731,303 A | 3/1998 | Hsieh | 514/183 |
| 5,736,577 A | 4/1998 | Aberg et al. | 514/617 |
| 5,783,207 A | 7/1998 | Stanley et al. | 424/440 |
| 5,785,991 A | 7/1998 | Burkoth et al. | 424/448 |
| 5,786,357 A | 7/1998 | Young et al. | 514/249 |
| 5,798,242 A | 8/1998 | Fujishiro et al. | 435/190 |
| 5,814,659 A | 9/1998 | Elden | 514/452 |
| 5,831,035 A | 11/1998 | Timms | 530/389.1 |
| 5,834,010 A | 11/1998 | Quan et al. | 424/448 |
| 5,843,482 A | 12/1998 | Rhodes et al. | 424/653 |
| 5,846,983 A | 12/1998 | Sandborn et al. | 514/343 |
| 5,855,905 A | 1/1999 | Oettel et al. | 424/426 |
| 5,855,920 A | 1/1999 | Chein | 424/568 |
| 5,891,462 A | 4/1999 | Carrara | 424/449 |
| 5,900,250 A | 5/1999 | Lee et al. | 424/448 |
| 5,904,931 A | 5/1999 | Lipp | 424/449 |
| 5,922,349 A | 7/1999 | Elliesen et al. | 424/449 |
| 5,925,372 A | 7/1999 | Berner et al. | 424/448 |
| 5,932,243 A | 8/1999 | Fricker et al. | 424/450 |
| 5,935,604 A | 8/1999 | Illum | 424/501 |
| 5,945,405 A | 8/1999 | Spanton et al. | 514/29 |
| 5,955,455 A | 9/1999 | Labrie | 514/178 |
| 5,968,919 A | 10/1999 | Samour | 514/177 |
| 6,008,192 A | 12/1999 | Al Razzak et al. | 514/11 |
| 6,034,079 A | 3/2000 | Sanberg et al. | 514/225.8 |
| 6,060,077 A | 5/2000 | Meignant | 424/434 |
| 6,071,959 A | 6/2000 | Rhodes et al. | 514/535 |
| 6,096,733 A | 8/2000 | Lubkin | 514/182 |
| 6,123,961 A | 9/2000 | Aberg | 424/468 |
| 6,124,355 A | 9/2000 | Guittard et al. | 514/534 |
| 6,133,248 A | 10/2000 | Stella | 514/58 |
| 6,153,216 A | 11/2000 | Cordes | 424/449 |
| 6,165,497 A | 12/2000 | Osborne et al. | 424/448 |
| 6,166,044 A | 12/2000 | Sandborn et al. | 514/343 |
| 6,180,803 B1 | 1/2001 | Piasco et al. | 552/150 |
| 6,238,689 B1 | 5/2001 | Rhodes et al. | 424/436 |
| 6,267,985 B1 | 7/2001 | Chen et al. | 424/451 |
| 6,284,234 B1 | 9/2001 | Niemiec | 424/78.07 |
| 6,299,900 B1 | 10/2001 | Reed et al. | 424/449 |
| 6,309,843 B1 | 10/2001 | Timms | 435/7.1 |
| 6,319,913 B1 | 11/2001 | Mak et al. | 514/179 |
| 6,383,471 B1 | 5/2002 | Chen et al. | 424/45 |
| 6,417,205 B1 | 7/2002 | Cooke et al. | 514/343 |
| 6,426,078 B1 | 7/2002 | Bauer et al. | 424/401 |
| 6,432,446 B2 | 8/2002 | Aberg | 424/468 |
| 6,440,454 B1 | 8/2002 | Santoro et al. | 424/449 |
| 6,444,234 B1 | 9/2002 | Kirby et al. | 424/725 |
| 6,451,300 B1 | 9/2002 | Dunlop et al. | 424/70.27 |
| 6,465,005 B1 | 10/2002 | Biali et al. | 424/449 |
| 6,476,012 B2 | 11/2002 | Hochberg | 514/182 |
| 6,479,076 B2 | 11/2002 | Blank | 424/484 |
| 6,497,897 B2 | 12/2002 | Hidaka et al. | 424/449 |
| 6,503,894 B1 | 1/2003 | Dudley | 514/178 |
| 6,545,046 B2 | 4/2003 | Sherratt et al. | 514/534 |
| 6,586,000 B2 | 7/2003 | Luo et al. | 424/449 |
| 6,596,740 B2 | 7/2003 | Jones | 514/343 |
| 6,743,441 B2 | 6/2004 | Sanders et al. | 424/448 |
| 6,818,226 B2 | 11/2004 | Reed et al. | 424/449 |
| 6,828,336 B2 | 12/2004 | Walling | 514/343 |
| 6,911,475 B1 | 6/2005 | Cesaro et al. | 514/567 |
| 6,923,983 B2 | 8/2005 | Morgan et al. | 424/448 |
| 6,929,801 B2 | 8/2005 | Klose et al. | 424/448 |
| 6,951,846 B2 | 10/2005 | Hartell et al. | 514/58 |
| 6,995,265 B2 | 2/2006 | Comins et al. | 546/14 |
| 7,029,692 B1 | 4/2006 | Bracht | 424/449 |
| 7,030,104 B2 | 4/2006 | Gray et al. | 714/170 |
| 7,087,241 B2 | 8/2006 | Sanders et al. | 424/449 |
| 7,198,801 B2 | 4/2007 | Carrara et al. | 424/449 |
| 7,214,381 B2 | 5/2007 | Carrara et al. | 424/449 |
| 2001/0023261 A1 | 9/2001 | Ryoo | 514/772 |
| 2001/0031787 A1 | 10/2001 | Hsu et al. | 514/534 |
| 2001/0033870 A1 | 10/2001 | Luo | 424/688 |
| 2001/0038855 A1 | 11/2001 | Desjardin et al. | 424/468 |
| 2002/0147236 A1 | 10/2002 | Sanders et al. | 514/540 |
| 2002/0183296 A1 | 12/2002 | Dudley et al. | 514/177 |
| 2003/0022877 A1 | 1/2003 | Dudley | 514/177 |
| 2003/0050292 A1 | 3/2003 | Dudley | 514/177 |
| 2003/0095926 A1 | 5/2003 | Dugger, III | 424/43 |
| 2003/0139384 A1 | 7/2003 | Dudley | 514/177 |
| 2003/0143278 A1 | 7/2003 | DiPiano et al. | 424/489 |
| 2003/0147926 A1 | 8/2003 | Ebert et al. | 424/400 |
| 2003/0175329 A1 | 9/2003 | Azarnoff et al. | 424/449 |
| 2003/0181430 A1 | 9/2003 | Gray et al. | 514/170 |
| 2003/0199426 A1 | 10/2003 | Carrara et al. | 514/2 |
| 2003/0222105 A1 | 12/2003 | Lee et al. | 222/382 |
| 2003/0232072 A1 | 12/2003 | Dudley et al. | 424/449 |
| 2004/0002482 A1 | 1/2004 | Dudley et al. | 514/169 |
| 2004/0139990 A1 | 7/2004 | Wachter et al. | 134/25.4 |
| 2004/0198706 A1 | 10/2004 | Carrara et al. | 514/169 |
| 2004/0213744 A1 | 10/2004 | Lulla et al. | 424/45 |
| 2004/0219197 A1 | 11/2004 | Carrara et al. | 424/449 |
| 2005/0142175 A1 | 6/2005 | Langguth et al. | 424/449 |
| 2006/0027278 A1 | 2/2006 | Kurmis | 140/123.5 |
| 2006/0153905 A1 | 7/2006 | Carrara et al. | 424/449 |
| 2007/0048360 A1 | 3/2007 | Carrara et al. | 424/443 |
| 2007/0098775 A1 | 5/2007 | Carrara et al. | 424/449 |
| 2007/0166361 A1 | 7/2007 | Carrara et al. | 424/448 |
| 2007/0225379 A1 | 9/2007 | Carrara et al. | 424/449 |
| 2009/0069364 A1 | 3/2009 | Carrara et al. | 514/284 |
| 2010/0216880 A1 | 8/2010 | Carrara et al. | 514/534 |

FOREIGN PATENT DOCUMENTS

| | | |
|---|---|---|
| EP | 0 261 429 A1 | 3/1988 |
| EP | 0 267 617 A1 | 5/1988 |
| EP | 0 271 983 A1 | 6/1988 |
| EP | 0 279 977 A2 | 8/1988 |
| EP | 0 325 613 B1 | 6/1989 |
| EP | 0 367 431 A1 | 5/1990 |
| EP | 0250125 B1 | 9/1991 |
| EP | 0 526 561 B1 | 2/1993 |
| EP | 0409383 B1 | 4/1994 |
| EP | 0491803 B1 | 7/1994 |
| EP | 0435200 B1 | 7/1995 |
| EP | 0 672 422 A1 | 9/1995 |

| | | | |
|---|---|---|---|
| EP | 785211 A1 | 7/1997 |
| EP | 785212 A1 | 7/1997 |
| EP | 0 811 381 A1 | 12/1997 |
| EP | 0804926 B1 | 10/1999 |
| EP | 0655900 B1 | 3/2000 |
| EP | 0719538 B1 | 11/2000 |
| EP | 0814776 B1 | 7/2001 |
| EP | 0643963 B1 | 11/2001 |
| EP | 0868187 B1 | 12/2001 |
| EP | 0859793 B1 | 2/2002 |
| EP | 1089722 B1 | 5/2002 |
| EP | 0802782 B1 | 2/2003 |
| EP | 1 323 430 A2 | 7/2003 |
| EP | 1 323 431 A2 | 7/2003 |
| EP | 1 325 752 A2 | 7/2003 |
| FR | 2518879 | 12/1981 |
| FR | 2 776 191 | 9/1999 |
| JP | 09176049 | 7/1997 |
| WO | WO 90/11064 A1 | 10/1990 |
| WO | WO 92/08730 | 5/1992 |
| WO | WO 94/06437 | 3/1994 |
| WO | WO 95/18603 A1 | 7/1995 |
| WO | WO 95/29678 A1 | 11/1995 |
| WO | WO 97/03676 | 2/1997 |
| WO | WO 97/29735 A1 | 8/1997 |
| WO | WO 97/34607 | 9/1997 |
| WO | WO 97/38726 | 10/1997 |
| WO | WO 98/17316 A1 | 4/1998 |
| WO | WO 98/37879 | 9/1998 |
| WO | WO 99/20257 | 4/1999 |
| WO | WO 99/24041 | 5/1999 |
| WO | WO 99/48477 | 9/1999 |
| WO | WO 01/80796 A1 | 11/2001 |
| WO | WO 02/11768 | 2/2002 |
| WO | WO 02/17967 A1 | 3/2002 |
| WO | WO 02/22132 | 3/2002 |
| WO | WO 2004/037173 A2 | 5/2004 |
| WO | WO 2004/080413 A2 | 9/2004 |
| WO | WO 2005/039531 A1 | 5/2005 |

OTHER PUBLICATIONS

C. Wang et al., "Transdermal Testosterone Gel Improves Sexual Function, Mood, Muscle Strength, and Body Composition Parameters in Hypogonadal Men," The Journal of Clinical Endocrinology & Metabolism, vol. 85(8):2839-2853 (2000).
U.S. Appl. No. 10/798,111, Non-Final Office Action dated Dec. 23, 2010.
U.S. Appl. No. 10/798,111, Non-Final Office Action dated Dec. 7, 2009.
U.S. Appl. No. 10/798,111, Non-Final Office Action dated Mar. 4, 2009.
U.S. Appl. No. 10/798,111, Non-Final Office Action dated Sep. 15, 2008.
U.S. Appl. No. 10/798,111, Non-Final Office Action dated Jun. 4, 2007.
U.S. Appl. No. 10/798,111, Non-Final Office Action dated Jan. 25, 2006.
U.S. Appl. No. 10/798,111 ,Non-Compliant Office Action dated Sep. 27, 2007.
U.S. Appl. No. 10/798,111, Final Office Action dated May 20, 2010.
U.S. Appl. No. 10/798,111, Final Office Action dated Jun. 5, 2009.
U.S. Appl. No. 10/798,111, Final Office Action dated Jun. 24, 2008.
U.S. Appl. No. 10/798,111, Final Office Action dated Jan. 12, 2007.
U.S. Appl. No. 10/798,111, Advisory Action dated Nov. 22, 2010.
U.S. Appl. No. 10/798,111, Advisory Office Action dated Sep. 9, 2009.
U.S. Appl. No. 11/755,923, Non-Final Office Action dated Oct. 12, 2010.
U.S. Appl. No. 11/755,923, Non-Final Office Action dated Feb. 22, 2010.
U.S. Appl. No. 11/755,923, Non-Final Office Action dated Mar. 19, 2009.
U.S. Appl. No. 11/755,923, Non-Final Office Action dated Nov. 17, 2008.
U.S. Appl. No. 11/755,923, Non-Final Office Action dated Jun. 24, 2008.
U.S. Appl. No. 11/755,923, Non-Final Office Action dated Mar. 10, 2008.
U.S. Appl. No. 11/755,923, Non-Final Office Action dated Sep. 7, 2007.
U.S. Appl. No. 11/755,923, Final Office Action dated Oct. 1, 2009.
U.S. Appl. No. 11/755,923, Final Office Action dated Jan. 25, 2008.
U.S. Appl. No. 11/755,923, Advisory Action dated Jan. 25, 2010.
U.S. Appl. No. 12/268,301, Non-Final Office Action dated Feb. 1, 2011.
G. Stüttgen, "Promoting penetration of locally applied substances by urea," Hautarzt 1989; 40 Suppl 9:27-31 (abstract).
Budavari et al., The Merck Index, 1996, Merck Research Laboratories, 12thEdition, pp. 253 and 269.
Kotiyan et al., "Eudragits:Role as crystallization inhibitors in drug-in-adhesive transdermal systems of estradiol," European Journal of Pharmaceutics and Biopharmaceutics 52: 173180 (2001).
Lipp, "Selection and use ofcrystallization inhibitors for matrixtype transdermal drug-delivery systems containing sex steroids," J. Pharm. Pharmacol. 50: 13431349 (1998).
Moser et al., "Passive skin penetration enhancement and its quantification in vitro," European Journal of Pharmaceutics and Biopharmaceutics 52: 103112 (2001).
Mura et al., "Evaluation of transcutol as a clonazepam transdermal permeation enhancer from hydrophilic gel formulations," European Journal of Pharmaceutical Sciences 9: 36-5372 (2000).
R. Panchagnula et al., "Development and evaluation of an intracutaneous depot formulation of corticosteroids using transcutol as a cosolvent: invitro, ex-vivo and in-vivo rat studies," J. Pharm. Pharmacol. 1991, 43: 609-614.
L. Pavliv et al., "Topical formulation development of a novel thymidylate synthase inhibitor for the treatment of psoriasis," International Journal of Pharmaceutics 1994, 105: 227-233.
W.A. Ritschel et al., "In vitroskin penetration of griseofulvin in rat and human skin from an ointment dosage form," Arzneimit-telforschung. 1988, 38(11): 1630-1632.
W.A. Ritschel et al., "Use of sorption promoters to increase systemic absorption of coumarin from transdermal drug delivery systems," Arzneimittelforschung. 1988, 38(12): 17741777.
W.A. Ritschel et al., "Development of an intracutaneous depot for drugs," Skin Pharmacol. 1991, 4:235-245.
J. Rojas, "Optimization of binary and ternary solvent systems in the perutaneous absorption of morphine base," S.T.P. Pharma Sciences 1991, 1(1): 70-75.
E. Touitou, "Enhanced permeation of theophylline through the skin and its effect on fibroblast proliferation," International Journal of Pharmaceutics 1991, 70: 159166.
A. Watkinson, "Aspects of the transdermal delivery of prostaglandins," International Journal of Pharmaceutics 1991, 74: 229-236.
M. Yazdanian et al., "The Effect of Diethylene Glycol Monoethyl Ether As a Vehicle for Topical Delivery OfIvermectin," Veterinary Research Communications 1995, 19(4): 309319.
English Abstract NLM2807923 XP-002337932 ,"Promoting Penetration of Locally Applied Substances by Urea",1989.
David W. Osborne et al., XP 002337808, "Skin Penetration Enhancers Cited in the Technical Literature", 1997.
A.C. Williams et al., XP 000645464,"Urea Analogues in Propylene Glycol As Penetration Enhancers in Human Skin", International Journal of Pharmaceutics, vol. 36, pp. 43-50 (1989).
Oxytrol Data Sheet, 2003.
Koichi Takahashi et al., "Effect of Vehicles on Diclofenac Permeation across Excised Rat Skin", Biol. Pharm. Bull., vol. 18, No. 4, pp. 571-575 (1995).
"New Drug Application: Elestrin, estradiol, Treatme for Postmenopausal Symptoms. BioSante Pharmaceuticals Announces Bio-E-Gel NDA Submission," Internet article, [online], Feb. 16, 2006; retrieved from the Internet: URL:http://www.drugs.com/nda/elestrin_060216.html (retrieved on Sep. 18, 2007).
P. Karande and S. Mitragotri, "High Throughput Screening of Transdermal Formulations," Pharmaceutical Research, 2002, 19(5): 655-660.
J. Fang et al., XP-0007999490, "Effect of Adhesive and Drug reservoir on in vitro transdermal delivery of Nocotine," Pharmazie; Die, Govi Verlag, Eschborn, De, (1999), 54(2): 154155.
US 6,214,374, 04/2001, Schmirier et al. (withdrawn)

Mean Change from Baseline in 4-Week Sexual Event Rate

Median Trough Serum Total T Concentrations

Median Trough Serum Free T Concentrations

METHOD AND APPARATUS FOR TRANSDERMAL OR TRANSMUCOSAL APPLICATION OF TESTOSTERONE

This application claims the benefit of provisional application No. 60/685,132 filed May 27, 2005, the entire content of which is expressly incorporated herein by reference thereto.

FIELD OF INVENTION

The present invention relates generally to a method, formulation and system for providing transdermal or transmucosal delivery of active agents to a subject. In particular, the invention relates to an improved method and formulation for treating female menopausal symptoms, female sexual desire disorder, and hypoactive sexual desire disorder. The invention also relates to a system for dispensing a precise dosage of a fluid medicament.

BACKGROUND OF THE INVENTION

Reduced levels of endogenous steroid hormones in humans often lead to a variety of undesirable clinical symptoms. For example, low testosterone levels in men (hypogonadism) may result in clinical symptoms including impotence, lack of sex drive, muscle weakness, and osteoporosis. Similarly, in women, reduced levels of testosterone and/or estrogen may result in female sexual disorder, which include clinical symptoms such as lack of sex drive, lack of arousal or pleasure, decreased energy levels or fatigue with blunted motivation, flat mood or depression, reduced sense of well-being, insomnia, irritability, partial decreases in vaginal lubrication, and osteoporosis. Moreover, reduced levels of estrogen and/or progesterone in women, such as that caused by menopause, often result in clinical symptoms including hot flashes, night sweats, vaginal atrophy, decreased libido, and osteoporosis.

The hormone testosterone (T) has historically been thought of as a male hormone, but it is also synthesized in women in small amounts, primarily by the ovaries and adrenal glands. The physiological functions ascribed to testosterone in women include: development of pubic and axillary hair as well as emerging sexual libido; anabolic effect on bone density and muscle tone; sexual libido; and overall vitality and sense of psychological well-being. Testosterone plasma concentrations in pre-menopausal women fluctuate during the menstrual cycle, with the total T plasma concentrations generally ranging between 15-65 ng/dL, but in the years leading to postmenopausal transition, levels of circulating androgens begin to decline as a result of age-related reductions of both ovarian and adrenal secretion. Generally, women with androgen deficiency have total T levels of less than 20-25 ng/dL, while oophorectomized women can have total T levels of less than 10 ng/dL. Thus, the goals of testosterone therapy are to restore plasma T levels so they approximate the premenopausal state and to alleviate the symptoms of Hypoactive Sexual Desire Disorder (HSDD) associated with T deficiency.

Currently, there are no testosterone products approved in the U.S. for treatment of HSDD in women. One transdermal testosterone matrix patch has been submitted for NDA approval for the treatment of HSDD, and Estratest™, an oral preparation containing methyltestosterone in combination with esterified estrogen, is approved for treatment of moderate-to-severe vasomotor symptoms associated with menopause, but not for HSDD.

Further, although steroid hormone concentrations may be restored to normal or near-normal levels by hormone replacement therapy, the current forms of treatment (i.e., oral, intramuscular, subcutaneous, transdermal patches and topical formulations) have several disadvantages.

For example, orally administered testosterone is largely degraded in the liver, and is therefore not a viable option for hormone replacement since it does not allow testosterone to reach systemic circulation. Further, analogues of testosterone modified to reduce degradation (e.g., methyltestosterone and methandrostenolone) have been associated with abnormalities in liver function, such as elevation of liver enzymes and conjugated bilirubin. Injected testosterone produces wide peak-to-trough variations in testosterone concentrations that do not mimic the normal fluctuations of testosterone, and makes maintenance of physiological levels in the plasma difficult. Testosterone injections are also associated with mood swings and increased serum lipid levels. Injections require large needles for intramuscular delivery, which leads to diminished patient compliance due to discomfort.

To overcome these problems, transdermal delivery approaches have been developed to achieve therapeutic effects in a more patient friendly manner. For example, U.S. Pat. No. 5,460,820 discloses a testosterone-delivering patch for delivering 50 to 500 μg/day of testosterone to a woman. In addition, U.S. Pat. No. 5,152,997 discloses a device comprising a reservoir of testosterone with a skin permeation enhancer and a means for maintaining the reservoir in diffusional communication with the skin, such as an adhesive carrier device or a basal adhesive layer. A transdermal patch or such other adhesive device, however, still presents disadvantages such as user discomfort, skin irritation due to the adhesive required to secure the patch to a pat of the user's body, and also the discomfort due to removal of the patch, during which both the user's skin and hair can be pulled.

The present invention addresses the problems associated with the known hormone replacement therapy by providing testosterone in a gel form for transdermal and/or transmucosal delivery. In this regard, an adhesive patch is not needed to administer the drug. Rather, the medicament is simply dispensed from a container and applied to an area of the skin. Accordingly, the present invention eliminates the discomforts caused by the conventional patch device.

Another significant advantage of the present invention is that since the user can simply apply the gel onto their skin, there is no application of an unsightly patch. Accordingly, the user can apply the gel to an area of skin that is visible to others. As the gel is absorbed into the skin, its "invisibility" provides a significant improvement over the conventional obstructive transdermal products which require external, non-discreet means of securing the product to the user. Thus, the present transdermal and/or transmucosal delivery of testosterone advantageously provides a convenient, pain-free, and non-invasive method of administering testosterone to a subject in need thereof.

Although administration of drugs in a gel form is favorable to users due to its pain-free and discreet administration, it has a drawback of difficulty in dispensing the proper dosage for administration. For example, it is known to provide medicaments in the form of gels, ointments, or lotions, in a tube, similar to the type of tube used to store toothpaste. Typically, the user is directed to squeeze the tube to dispense the ointment or gel containing the drug in a specific amount, such as an inch on a finger tip, or some other type of length. This is problematic especially because it requires careful dispensing of the medicament, and precise measuring on the part of the user to ensure administration of the proper dosage. Often-times users over- or under-dose themselves due to carelessness or simply because it is difficult to measure the amount of medicament dispensed from the particular tube. Accordingly, administering an accurate dosage amount of a gel-type medicament from such containers is difficult, and usually only a ballpark measure can be dispensed.

Thus, a method and system for administering gel-type medicaments in a precise, metered amount is desired. The present invention meets this need by providing a gel-like medicament in combination with a metered dosage device. The metered dosage device dispenses an amount of medicament that corresponds to a particular dosage. Accordingly, active agents in a gel-like form can be applied in the desired dosage for effective treatment.

SUMMARY OF THE INVENTION

The present invention generally relates to a method, formulation and system for providing transdermal or transmucosal testosterone replacement therapy to female subjects.

In accordance with one aspect of the invention, a method is provided for providing testosterone replacement therapy to a female subject in need. The method comprises administering testosterone to a female subject in an effective amount up to about 2.4 mg, and preferably about 2.2 mg daily. The present method may be used to treat menopausal females, including surgically menopausal and naturally menopausal females, as well as pre-menopausal females with low testosterone levels. The term "low testosterone level" as used herein means a testosterone level that is less than 50% of the normal testosterone level for females. The normal range of total testosterone in a female is between about 10 to 55 ng/dl and the normal range of free testosterone levels in a female is between about 1.1 to 6.3 pg/ml. Advantageously, the present method has been found to decrease or alleviate clinical symptoms of hormonal disorders related to testosterone deficiency, such as but not limited to hypoactive sexual desire disorder (HSDD) and female sexual dysfunction (FSD).

In another aspect of the invention, the testosterone is administered conveniently in the form of a transdermal or transmucosal formulation. In this manner, the testosterone formulation can further include an alkanol, for example, a $C_2$ to $C_4$ alcohol such as ethanol, isopropanol, and/or n-propanol, in an amount between about 5 to 80%; a polyalcohol such as polypropylene glycol in an amount between about 1% to 30%; and a permeation enhancer, such as diethylene glycol monomethyl ether or diethylene glycol monoethyl ether in an amount between about 1 to 30% by weight. The gel formulation in accordance with the invention facilitates the absorption of testosterone by the subject's dermal or mucosal surfaces, and minimizes the transfer or removal of the formulation from the user's skin after application.

In a preferred embodiment, the alkanol is provided in combination with water to form a hydroalcoholic mixture. Preferably, the alkanol comprises about 5% to 80% and the water comprises about 20% to 95% of the mixture by weight. The hydroalcoholic mixture may be present in an amount of about 40 to 98% by weight of the formulation.

The formulation may further comprise at least one of a gelling agent, neutralizing agent, buffering agent, moisturizing agent, humectant, surfactant, antioxidant, emollient, or buffer, and may be provided in the form of a gel, lotion, cream, ointment, emulsion, or suspension. Preferably, the testosterone formulation is provided as a gel.

In accordance with a further aspect of the invention, the testosterone formulation can be dispensed from a metered dosage device to provide convenience as well as precise metered dosages to users. Accordingly, the metered dosage device can be configured to dispense a precise amount of the testosterone formulation which corresponds to a desired and prescribed dosage of testosterone to the user.

In accordance with another aspect of the present invention, a system is provided for dispensing a precise amount of a medicament. The system comprises a storage unit for retaining the medicament and a dispenser unit for releasing a predetermined amount of the medicament upon activation by a user. In further accordance with the invention, one embodiment includes a pressure-operable pump, such as a finger-operable pump, which may be activated by a user. In this regard, the user can simply depress the finger-operable pump to cause the metered dosage pump to dispense a metered amount of the medicament when the pump is pressed by the user. In this regard, the self-administration of a precise dosage of medicaments in the form of a topical formulation such as a gel, lotion, or ointment, is easy and convenient.

The medicament may include any active agent suitable for topical or transdermal administration. For example and not limitation, the active agent can include steroid hormones such as testosterone, estrogen, and progestin.

The medicament is preferably in the form of a gel, ointment, cream, lotion, or other suitable form for dispensing from a metered dosage dispenser. In one embodiment, the metered dosage dispenser can be configured to advantageously releases an predetermined amount of medicament sufficient to administer up to about 2.4 mg of testosterone when activated by a user. Alternatively, the metered dosage device can be configured to dispense other effective amounts or dosages of medicament, as prescribed for the user. In this manner, and for example and not limitation, the dosage device can be configured to dispense a specific amount of gel, ointment or lotion corresponding to a specific dosage of medicament based on the concentration of the medicament. For example, in one embodiment, the dosage device for example and not limitation can be configured to dispense about 0.10 to 0.5 grams of gel containing 1% testosterone. Therefore, the present invention provides for topical administration of testosterone in a precise, metered amount. Accordingly, the invention also relates to an improvement in administering medicaments including testosterone to a subject in need thereof. The improvement comprising accurately controlling the administration of a medicament formulation to the subject by dispensing the formulation from a metered dosage device.

BRIEF DESCRIPTION OF THE DRAWINGS

The features and benefits of the invention will now become more clear from a review of the following detailed description of illustrative embodiments and the accompanying drawings, wherein.

DETAILED DESCRIPTION OF THE PREFERRED EMBODIMENTS

Figure 1:
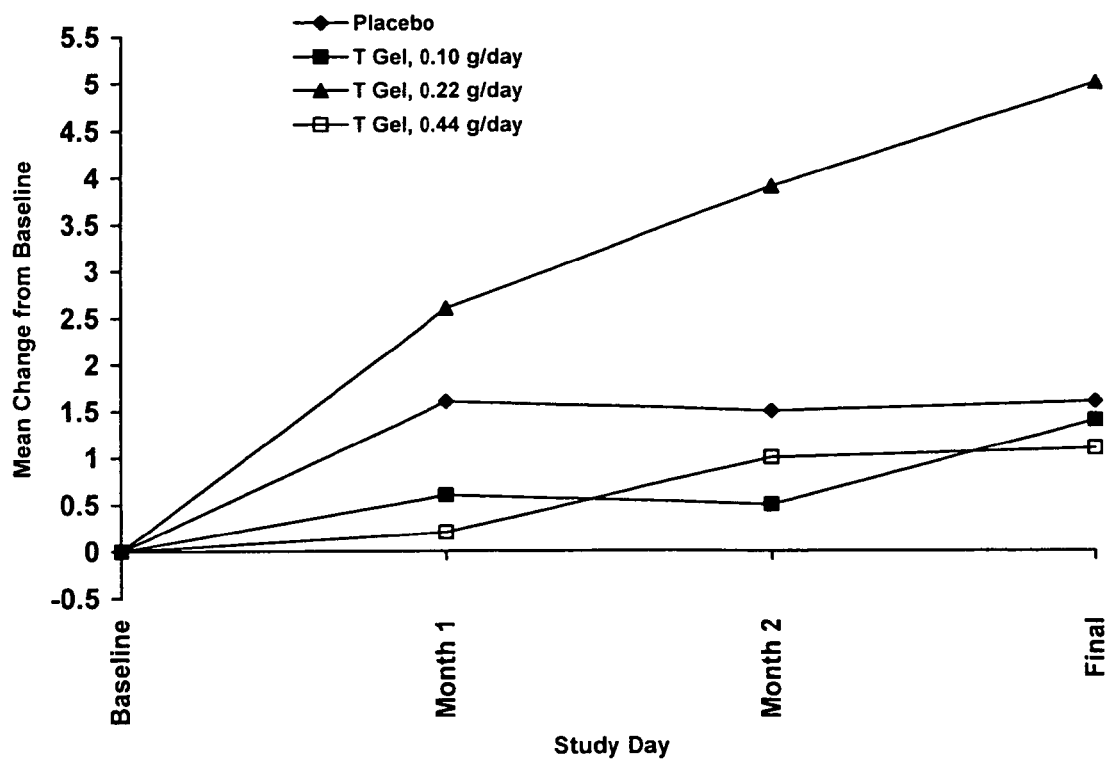
FIG. 1 is a graphic representation of mean change from baseline in 4-week sexual event rate during the administration of different doses of the present testosterone gel formulation compared to placebo.

The present invention relates to a method, formulation and system for providing transdermal or transmucosal delivery of active agents to subjects, and in particular to an improved method and formulation for treating hormonal disorders such as female menopausal symptoms in both surgically menopausal and naturally menopausal females, pre-menopausal females having low testosterone levels, and females having female sexual desire disorder, and/or hypoactive sexual desire disorder (HSDD).

As to the methods for treating hormonal diseases, disorders, or conditions in a subject in need of such treatment, the method generally comprises administering a formulation comprising an effective dosage of testosterone.

In one preferred embodiment of the invention, the method comprises administering to a subject in need of such treatment a transdermal formulation comprising up to about 2.4 mg of testosterone. The formulation may further comprise an alkanol, a polyalcohol, and a permeation enhancer in an amount sufficient to provide permeation enhancement of testosterone through mammalian dermal or mucosal surfaces.

The present method can be used to decrease the frequency and/or severity of at least one of the clinical symptoms of the hormonal disorder being treated. For example, administration of the present formulation is helpful in decreasing the frequency and/or severity of symptoms such as hot flashes, night sweats, decreased libido, and osteoporosis, to name just a few.

For the purpose of illustration and not limitation, and in accordance with the invention, for example, a woman undergoing treatment may be of childbearing age or older, in whom ovarian androgen production has been interrupted either because of natural menopause, surgical procedures, radiation, chemical ovarian ablation or extirpation, or premature ovarian failure. In addition to natural menopause and aging, a decline in total circulating androgens leading to testosterone deficiency can be attributed to conditions that suppress adrenal androgen secretion (i.e., acute stress, anorexia nervosa, Cushing's syndrome, and pituitary renal insufficiency), conditions that can decrease ovarian androgen secretion (i.e., ovarian failure and the use of pharmacologic doses of glucocorticoids), and chronic illness such as muscle-wasting diseases like Acquired Immune Deficiency Syndrome (AIDS). Thus, the term "hormonal disorder" as used herein means any condition that causes a suppression or reduction of hormonal secretions in a subject.

In addition to treating female subjects for female menopausal symptoms due to aging and other factors as discussed above, reduced levels of androgens in women may lead to female sexual dysfunction (FSD) resulting in clinical symptoms such as lack of sex drive, arousal or pleasure; low energy, reduced sense of well-being and osteoporosis. Preferred results of using the formulations of the present invention to treat FSD in women may include one or more of the following: increased energy, increased sense of well-being, decreased loss of calcium from bone, and increased sexual activity and desires.

In pre-menopausal women, total plasma testosterone concentrations generally range from 15-65 ng/dL (free testosterone in pre-menopausal women is approximately 1.5 to 7 pg/ml) and fluctuate during the menstrual cycle, with peaks of androgen concentration corresponding to those of plasma estrogens at the pre-ovulatory and luteal phases of the cycle. In the years leading to postmenopausal transition, levels of circulating androgens begin to decline as a result of age-related reductions of both ovarian and adrenal secretion. There are reports in studies that 24-hour mean plasma testosterone levels in normal pre-menopausal women in their 40's are half that of women in their early 20's. It has been generally accepted, however, that women with androgen deficiency have total testosterone levels less than 25 ng/dL (<50-years-old) or less than 20 ng/dL ($\geq$50-years-old) while oophorectomized women can have total testosterone levels less than 10 ng/dL.

In this regard, the method may include administering to the female subject a therapeutically effective dosage of testosterone from of about up to 2.4 mg may be provided daily. Such dose is particularly effective in treating menopausal women, including surgically menopausal women who have undergone oophorectomy. Therefore, the formulation preferably provides the subject with a total serum concentration of testosterone from at least about 15 to about 55 ng/dL, or a free serum concentration of testosterone from about 2 to about 7 pg/mL.

A study of women who were surgically menopausal showed significant improvements in sexual sensation and desire 12 weeks of present testosterone treatment versus placebo treatment or testosterone treatment with different testosterone doses. To achieve good response in terms of libido, plasma testosterone levels need to be restored to about at least the upper end of the normal physiologic range observed in young ovulating women. In surgically menopausal women, administration of the present transdermal testosterone gel improved sexual function and psychological well-being.

In accordance with another aspect of the invention, a method is provided for providing hormone treatment therapy to a subject need. The method includes administering an effective amount of testosterone in the form of a gel to a subject in need. The subject may be male or female. For example and not limitation, a male subject can be treated for hypogonadism and a female can be treated for low sexual desire. The testosterone gel further includes an alkanol, a polyalcohol, and optionally a permeation enhancer, as described below. In a preferred embodiment, the testosterone is present in an amount of about 1.05 by weight of the gel. Advantageously, the gel is applied to a transdermal or transmucosal surface such as the skin of the subject. No occlusive device, such as a patch, is needed.

The preferred dosages of the present method are capable of delivering an effective amount of testosterone over a period of about 24 hours. By an "effective" or "therapeutically effective" amount of testosterone is meant a nontoxic, but sufficient amount of the agent to provide the desired effect.

In accordance with the present invention, the effective amount of testosterone may be provided in clear, water washable, cool to the touch, quick drying, spreadable and/or a non-greasy formulations, such as a gel, or similar fluid formulations such as but not limited to a cream, lotion, ointment, or suspension, which can be applied directly to the skin. The present transdermal or transmucosal testosterone replacement therapy provides important advantages over the known oral, intramuscular, and transdermal products by advantageously delivering serum testosterone concentrations that are not subject to first-pass metabolism and avoiding wide swings in serum testosterone concentrations while reducing skin reactions often observed with existing transdermal patch products.

In the following description, the term "mammal" is used to include all warm-blooded mammals, preferably humans. The term "mucosa" as used herein means any moist anatomical membrane or surface on a mammal such as oral, buccal, vaginal, rectal, nasal or ophthamalic surfaces. The term "topical" or "topically" is used herein in its conventional meaning as referring to direct contact with an anatomical site or surface area on a mammal including skin, mucosa, teeth, and nails.

The term "excipient" as used herein refers to an inert substance combined with an active agent such as a local anesthetic agent or penetration enhancer to prepare a convenient dosage form and vehicle for delivering the active agent. The term "active agent" is used herein to refer to a substance or formulation or combination of substances or formulations of matter which, when administered to an organism (human or animal) induces a desired pharmacologic and/or physiologic effect by local and/or systemic action.

The term "low testosterone level" as used herein means a testosterone level that is less than 50% of the normal testosterone level for females. The normal range of total testosterone in a female is between about 10 to 55 ng/dl and the normal range of free testosterone levels in a female is between about 1.1 to 6.3 pg/ml.

The term "surgically menopausal women" includes women who have undergone oophorectomy. The terms "dose" and "dosage" mean a specific amount of active or therapeutic agents for administration. The terms "DHT" means dihydrotestosterone; "DHEA-S" is dehydroepiandrosterone-sulfate; $E_1$ is estrone; $E_2$ is estradiol; "FSH" is follicle stimulating hormone; and "SHBG" means sex hormone-binding globulin.

The transdermal formulation may further comprise a delivery vehicle of an alkanol, preferably, a $C_2$ to $C_4$ alkanol and a polyalcohol, and a permeation enhancer of monoalkyl ether of diethylene gylcol, in an amount sufficient to provide permeation enhancement of the active agent through mammalian dermal or mucosal surfaces, and optionally water. Accordingly, the present testosterone formulation may comprise one or more delivery vehicles or excipients such as alkanol and polyalcohol. Such excipients provide a convenient dosage form and vehicle for delivering testosterone. Pharmaceutically acceptable, preferably liquid, excipients which do not substantially negatively affect the properties of the present gel formulation may be used.

In one preferred embodiment, the alkanol is present in an amount of about 5 to 80% and the polyalcohol is present in an amount of about 1 to 30%, by weight of the formulation. The alkanol is preferably a $C_2$ to $C_4$ alcohol, for example and not limitation ethanol, isopropanol, and n-propanol. The polyalcohol is preferably polypropylene glycol, dipropylene glycol, or mixtures thereof. The alkanol may be provided in combination with water to form a hydroalcoholic mixture, if desired. Preferably, the hydroalcoholic mixture is present in an amount of about 40 to 98% by weight of the formulation. In this regard, the alkanol may comprise about 5 to 80% of the hydroalcoholic mixture by weight, and the water about 20 to 95% by weight. However, as known in the art, the amount of the alcoholic component of the formulation may be selected to maximize the diffusion of the active agent testosterone through the skin while minimizing any negative impact on the active agent itself or desirable properties of the formulation.

The formulation may further include a permeation agent if desired. Suitable permeation enhancers have no irritancy or toxicity to the skin, and enhance permeation of an active agent across the skin. In this regard, skin differs from soft and moist mucosa in that it contains a dense stratum corneum of keratinized cells, as well as the epidermal cell layer. Both layers act to restrain the percutaneous penetration of topically applied substances. Additionally, the skin has a superficial, cutaneous layer (the horny layer) which consists of flat, scale-like "squames" made up of the fibrous protein keratin. Accordingly, the inclusion of a permeation agent assists permeation by overcoming the skin barrier to the testosterone.

Preferably, the permeation enhancer is physiochemically stable and does not have pharmacologic effects and preferably should not have a disagreeable smell, color or taste. Suitable Permeation enhancers are described in detail in Remington's Pharmaceutical Sciences, Vol. 18, Mack Publishing Co., Easton, Pa. (1990), in particular Chapter 87, the entire contents of which are incorporated herein by reference. For example and not limitation, suitable permeation enhancers include monoalkyl ether of diethylene glycol such as diethylene glycol monomethyl ether, diethylene glycol monoethyl ether, or mixtures thereof.

The selection of the permeation enhancer can affect the amount and rate of transdermal or transmucosal absorption of the present testosterone formulation. The amount of the permeation enhancer may be optimized. In a preferred embodiment, the permeation enhancer may comprise about 1 to 30% of the formulation by weight.

The formulation may further comprise a gelling agent, neutralizing agent, buffering agent, moisturizing agent, humectant, surfactant, antioxidant, emollient, and/or buffer, and may be provided in the form of a gel, lotion, cream, ointment, emulsion, or suspension.

Gelling Agent. Thus, the present formulation may further include a thickening agent or gelling agent present in an amount sufficient to alter the viscosity of the formulation. A gelling agent can be selected from the group including: carbomer, carboxyethylene or polyacrylic acid such as Carbopol 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, Methocel grades; natural gums such as arabic, xanthan, guar gums, alginates; polyvinylpyrrolidone derivatives such as Kollidon grades; and polyoxyethylene polyoxypropylene copolymers such as Lutrol F grades 68, 127. Other gelling agents may include chitosan, polyvinyl alcohols, pectins, and veegum grades.

Preferably, the gelling agent is Lutrol F grades and Carbopol grades. The gelling agent may be present from about 0.2 to about 30.0% w/w depending on the type of polymer. More preferably, the gelling agent includes about 0.5%-5% by weight of a thickening agent. The amount of the gelling agent in the formulation may be selected to provide the desired product consistency and/or viscosity to facilitate application to the skin.

Preservatives. The formulation may further include preservatives such as but not limited to benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative may be present from about 0.01 to about 10.0% w/w of the formulation depending on the type of compound.

Antioxidant. The formulation may optionally include antioxidants such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant may be present from about 0.001 to about 5.0% w/w of the formulation depending on the type of compound.

Buffers. The formulation may further include buffers such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art may be included. The buffer may replace up to 100% of the water amount within the formulation.

Humectant. The formulation may further include humectant, such as but not limited to glycerin, propylene, glycol, sorbitol, triacetin. The humectant may be present from about 1 to 10% w/w of the formulation depending on the type of compound.

Sequestering Agent. The formulation may further include a sequestering agent such as edetic acid. The sequestering agent is present from about 0.001 to about 5% w/w of the formulation depending on the type of compound.

Surfactant. The formulation may further include anionic, non-ionic or cationic surfactants. The surfactant may be present from about 0.1% to about 30% w/w depending on the type of compound.

pH Regulator. Optionally, the formulation may include a pH regulator, generally, a neutralizing agent, which can optionally have crosslinking function. By way of example and not limitation, the pH regulator may include a ternary amine such as triethanolamine, tromethamine, tetrahydroxypropylethylendiamine, NaOH solution. The pH regulator may be present in the formulations in about 0.05 to about 2% w/w.

Moisturizers and Emollients. Optionally, the formulation may include moisturizers and/or emollients to soften and smooth the skin or to hold and retain moisture. By way of example and not limitation, moisturizers and emollients may include cholesterol, lecithin, light mineral oil, petrolatum, and urea.

For any particular formulation, these other ingredients may be selected to achieve the desired drug delivery profile and the amount of penetration desired. The optimum pH may also be determined and may depend on, for example, the base and degree of flux required.

The present transdermal/transmucosal formulation may be prepared by ordinary production methods. For example, the active agent testosterone, permeation enhancer, excipient(s) may be introduced into a standard preparation vessel and mixed to form a homogeneous composition.

The present formulation may be applied once daily, or multiple times per day depending upon the condition of the patient. The formulation of the invention may be applied topically to any body part, such as the thigh, abdomen, shoulder, and upper arm. In one embodiment, a formulation in the form of a gel is applied to about a 5 inch by 5 inch area of skin. Application may be to alternate areas of the body as applications alternate. For example, the gel may be applied to the thigh for the first application, the upper arm for the second application, and back to the thigh for the third application. This may be advantageous in alleviating any sensitivity of the skin to repeated exposure to components of the formulation.

The present invention, therefore, provides an improved method of providing testosterone hormone replacement therapy in a manner that is not only clinically effective but also user-friendly. Not only does the present method provide an effective dosage of testosterone, but it also enables easy administration and compliance by patients, since the present transdermal/transmucosal testosterone formulation is easy and painless to apply. Furthermore, as the present formulation is absorbed into the patient's skin or mucosa, it is "invisible" after application, and therefore much more discreet than the conventional patch products that have been used for transdermal testosterone delivery. Manufacturers will also appreciate that the present formulation is more cost-effective to produce as it does not require extra steps and materials, such as adhesives and fabrics which are required for production of traditional patch products. Accordingly, the present testosterone formulation and method provide numerous advantages over the existing testosterone replacement therapy products both for the consumer and the manufacturer.

After preparation, the present formulation can be transferred to a suitable packaging container. A metered dosage device may preferably be used as the packaging container.

Thus, the present invention also relates to a metered dosage system which comprises a storage unit for retaining a medicament containing an active agent and a dispenser unit for releasing a predetermined amount of the medicament upon activation by a user. Preferably, the dispenser unit comprises a pressure-operable pump, which dispenses a metered dosage of the active agent upon activation by a user.

The storage unit may be any one of various rigid or flexible receptacles such as bottles, tubes or pots, and the dispenser unit may be mounted on the storage unit by any conventional means, such as by a screw, snap-fit, or welded connection. The size of the storage unit may vary, depending on the intended use. For example, a large container may be used in laboratories or doctor's offices, while a smaller unit may be preferred for home use.

Advantageously, the present system or device can handle fluid medicaments of different viscosities, ranging from liquid products to products with creamy consistency. The device may have an appropriately sized opening that is capable of dispensing an amount of the medicament without being clogged.

According to a preferred embodiment, the dispenser unit comprises a pressure-operable pump, such as a finger-operable pump, which is commonly used to dispense lotions. Such pressure-operable pumps are particularly advantageous for dispensing fluid or liquid topical formulations for their convenience and ease of use, as they do not require opening or closing the container cap or lid or squeezing the container to dispense the product. Moreover, since the present metered dosage system enables dispensing the fluid medicament without having to open the cover or lid of the container, it minimizes the problems associated with storing a medicament in a conventional lid-cover container, such as oxidation of the active ingredient and contamination or spoilage of the medicament.

Hence, by providing the pressure-operable pump feature that is also capable of dispensing a predetermined amount, the present invention allows an improved way of dispensing a precise amount of fluid medicaments. Where the medicament contains a certain concentration of an active ingredient, the present metered dosing device can be used to dispense a precise dosage of the active ingredient. For example, when used in combination with a gel containing 1% testosterone, the present device may be designed to dispense 0.2 g of the gel when activated by pressure, e.g., by pressing on the pump, such that about 2 mg of testosterone is dispensed. Thus, the present device may be conveniently used for self-administration of a precise testosterone dosage, and may be designed to provide the preferred dosage amount, such as up to about 2.4 mg of testosterone, according to the present method for testosterone hormone replacement therapy. When smaller doses are to be applied more often, the device can be designed to dispense 1.0 or even 0.5 mg of testosterone upon each activation. Thus, a four 0.5 mg doses, two 1 mg doses or a single 2 mg dose can be administered to provide the preferred amount of 2 mg of testosterone each day.

In addition to the metered dosage device described above, a sachet with a metered amount of active ingredient or other metered dosage devices can also be used.

The present invention, therefore, provides an improved way of dispensing and administering a drug in a gel or ointment form by enabling easy and convenient administration of the proper dosage, and eliminates the problems of user over- or under-dose that were common in the conventional gel-type drug administration. Even the most inexperience users can follow a treatment regime that requires precise drug dosage administration.

While the present device has been described mostly with respect to a gel-type medicament containing testosterone, it will be appreciated that the device may be used in combination with any fluid composition. Because of its capability to dispense a precise, predetermined amount of medicament with a concentration of an active agent, however, the present device is particularly advantageous for dispensing and administering a specific amount of active agents. Where the active agent is a hormone, such as testosterone, the present device can be used to provide a convenient and reliable hormone replacement regime.

EXAMPLES

The following example is illustrative only and should not be interpreted as limiting.

Example 1

Comparative Study of T Gel Formulation Doses

To test the efficacy of the present gel formulation delivery, a comparative study was designed to detect a clinically significant difference in serum T concentration and 4-week satisfying sexual event rate. The study was conducted with 46 surgically menopausal women with a serum free T≦1.5 pg/mL, who were on a stable dose of conjugated estrogen of at least 0.625 mg/day or an equivalent oral estrogen for at least two months, and consisted of an 8-week pretreatment period and a 12-week double-blind treatment period (Days 1 to 85). At Day 1, eligible subjects were equally randomized to one of four treatment arms: 0.10 g/day (1.0 mg T/day), 0.22 g/day (2.2 mg T/day), or 0.44 g/day (4.4 mg T/day) of the present gel formulation with 1% testosterone (hereafter denoted as "T Gel"), or a matching placebo gel. Subjects returned for safety and efficacy evaluations every 4 weeks, and serum trough hormone samples were drawn at each visit. The following three testosterone dosage strengths of the present gel formulation were investigated in the study.

TABLE 1

| | Dosage Strengths | |
|---|---|---|
| Amount of T Gel Applied | Dose of Testosterone Applied | Nominal Daily Testosterone Dose |
| 0.10 g | 1.0 mg | 75 mcg/day |
| 0.22 g | 2.2 mg | 150 mcg/day |
| 0.44 g | 4.4 mg | 300 mcg/day |

Each subject was provided with and instructed to complete a diary to record daily sexual events and encounters and a sexual desire score using a visual analog scale. The subject was instructed to record these events for 8 weeks of the pretreatment period and throughout the treatment. The daily diary was used to record sexual events and encounters, the level of sexual interest or desire using a visual analog scale, as well as time of study drug application beginning on Day 1. Each successful and satisfying sexual event and encounter was recorded in the diary. In addition to satisfying sexual events and encounters, the subject's level of sexual interest or desire was recorded using a visual analog scale provided in the daily diary. The subject was instructed to make a mark indicating the level of sexual interest or desire for that day, using the following visual analog scale:

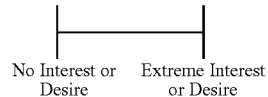

The scale used was 100 mm in length and subjects were instructed to make a single vertical mark through the line. The mark was measured by data management. If a mark fell between two consecutive millimeter measures, the higher measurement was used.

Blood samples for determination of trough serum concentrations for total, free, and bioavailable T, DHT, and SHBG were obtained at Days 1, 29, 57 and 85 (final visit). Additionally, blood samples for DHEA-S, $E_2$, $E_1$, and FSH were collected at Days 1 and 85 (Final Visit). Subjects were reminded not to apply study drug at home prior to the visit. At each visit, the blood samples were to be drawn 15 minutes prior to the scheduled study drug application for that day. The blood draw time was recorded on the appropriate report form.

The primary efficacy endpoint for comparing the treatments in this study was change from baseline in 4-week sexual event rate to Day 85/Final Study Visit, defined as the day subsequent to day of the last completed daily diary record or the day subsequent to the day of the last dose of randomized study drug, whichever is earlier. The primary efficacy comparison was based on this primary endpoint.

The baseline 4-week sexual event rate for each subject was calculated as the total number of successful sexual events (i.e., satisfactory sexual intercourse with or without orgasm, receiving oral sex with or without orgasm, and partner-initiated or self masturbation with or without orgasm) recorded in the diary during the Pretreatment Phase, multiplied by the ratio of 28 days (4 weeks) to the actual number of days in the Pretreatment Phase. For example, if a subject had 3 successful sexual events recorded during a 56-day (8 week) Pretreatment Phase, the calculated baseline 4-week sexual event rate would be 1.5 (3 times the ratio 28/56). Absence of a daily diary record for any given day in the Pretreatment Phase was interpreted as no successful sexual event for that day.

For a given study day on or after Day 29 of the Treatment Phase, the 4-week sexual event rate for each subject was simply the total number of successful sexual events (i.e., satisfactory sexual intercourse with or without orgasm, receiving oral sex with or without orgasm, and partner-initiated or self masturbation with or without orgasm) recorded in the diary during the 28-day period immediately preceding that day. For a given study day from Day 1 to Day 28 of the Treatment Phase, say Day X, the 4-week sexual event rate for each subject was calculated as the total number of successful sexual events recorded in the diary during the period from Day 1 to Day X−1, multiplied by the ratio of 28 days (4 weeks) to X−1. For example, if a subject had 6 successful sexual events recorded during Days 1 to 14, the calculated 4-week sexual event rate at Day 15 is 12.0 (6 times the ratio 28/14). For calculation purposes, the Treatment Phase began on the day the subject is administered the first dose of randomized study drug, and ended on the day subsequent to day of the last completed daily diary record or the day subsequent to the day of the last dose of randomized study drug, whichever was earlier. Absence of a daily diary record for any given day in the Treatment Phase was interpreted as no successful sexual event for that day.

Blood samples for determination of trough serum total, free, and bioavailable testosterone, DHT, and SHBG concentrations were obtained prior to randomization and at each study visit during the Treatment Period. Trough serum DHEA-S, estradiol, estrone, and FSH were collected prior to randomization and Final Visit. Subjects were not to apply study drug prior to any of these visits. To prevent contamination of the blood/serum samples with exogenous testosterone, the individual who was collecting or processing the blood sample was instructed to not handle study drug gel prior to and during sample collection or processing of the blood sample. The area of the subject's skin where study gel was applied was to be avoided during blood sample collection as much as possible.

Total testosterone circulates in three forms. A bound fraction is divided between testosterone that is strongly bound to SHBG and a weakly bound fraction that is bound to serum albumin. The third and smallest form is the free or unbound fraction. The free form may be the biologically most important since it represents the testosterone which is most available to diffuse into cells and exert biological activity.

Total testosterone was measured by two different methods. The screening (Day-56) total testosterone was measured using radioimmunoassay (RIA) after nonpolar solvent extraction and alumina column chromatography. All subsequent measurements (from Baseline (Day 1) to Final Visit) of total testosterone were measured by liquid chromatography with mass spectrometry (LC-MS) detection after nonpolar solvent extraction. Cross validation was completed and the LC-MS method showed good agreement with the RIA method both in the controls as has been demonstrated previously and using clinical samples that were previously run by RIA. The average bias for the LC-MS method versus the RIA was 3.0%.

Free T is measured by equilibrium dialysis. Serum is dialyzed overnight with mixing against buffer so that $^3$H-testosterone equilibrates between the serum and dialysate. An aliquot of the serum and an aliquot of the dialysate are counted in a beta scintillation counter. The free fraction is calculated from the corrected ratio of the two levels of radioactivity. The dialysate is tested for protein level to rule out leakage of the serum into the buffer. Serum Free T is calculated by multiplying the fraction free times the total testosterone with unit corrections.

Bioavailable testosterone is measured by ammonium sulfate precipitation of the strongly bound form of testosterone. The bioavailable fraction includes the free and the weakly bound forms of testosterone. The SHBG-bound-testosterone precipitates with the SHBG in 50% saturated ammonium sulfate solution, and the supernatant contains the bioavailable fraction.

Sex hormone binding globulin (SHBG) was measured using an immunoradiometric assay (IRMA) developed, validated and performed at Esoterix, Inc. (Calabasas Hills, Calif.). A monoclonal antibody made to human SHBG is coated onto plastic beads. The sample and a different SHBG monoclonal antibody that is labeled with $^{125}$I are incubated overnight with the antibody-coated bead. SHBG in the sample or standard forms BEAD-ANTIBODY-SHBG-ANTIBODY$^{125}$I sandwiches, attaching label to the beads. The beads are washed to remove unbound label, and counted. All samples are assayed in duplicate.

DHT was measured by radioimmunoassay after extraction and oxidation. Samples are extracted with Hexane:Ethyl Acetate (90:10). The extract is treated to a proprietary oxidation step that removes more than 99% of testosterone in the sample. DHT is then measured by radioimmunoassay.

DHEA-S was measured using an enzymatic hydrolysis followed by a liquid phase, competitive radioimmunoassay procedure. Samples are treated to enzymatic hydrolysis by a sulfatase that liberates DHEA from DHEA-S. The sample is then incubated with antibody and $^3$H-DHEA. After separating the % free from bound $^3$H-DHEA the mass of DHEA is interpolated from the standard curve. This concentration is corrected by the molecular weight ratio of DHEA-S to DHEA to arrive at the DHEA-S concentration.

Estradiol was measured by radioimmunoassay after extraction and LH20 column chromatography. Samples are extracted with hexane:ethyl Acetate (80:20). The extract is then washed with dilute base, concentrated and applied to LH20 micro columns.

Estrone was measured by radioimmunoassay after extraction and LH20 column chromatography. Samples are extracted with hexane:ethyl Acetate (80:20). The extract is then washed with dilute base, concentrated and applied to LH20 micro columns.

Follicle Stimulating Hormone (FSH) was measured by a two-site immunochemiluminometric assay (ICMA).

The mean increases from baseline in 4-week satisfying sexual event rate were observed for all four treatment groups, with a more pronounced increase observed in the T gel 0.22 g/day (2.2 mg T/day) dose group (see Table 2). A statistically significant difference (p=0.046) was observed between the T gel 0.22 g/day and placebo groups in the mean increase in 4-week satisfying sexual event rate at Day 85 (final study day) (difference between group=3.4). Although not significantly different than placebo at Day 85 (final study day), the T gel 0.1 g/day (1.0 mg T/day) and 0.44 g/day (4.4 mg T/day) doses showed an increase in 4-week satisfying sexual event rate of 1.4 and 1.1, respectively. Table summarizes the mean change from baseline in 4-week satisfying sexual event rate. The results are also graphically shown in FIG. 1.

TABLE 2

Mean Change from Baseline in 4-Week Satisfying Sexual Event Rate (ITT-LOCF)

| Evaluation | Mean Change from Baseline[a] | | | |
|---|---|---|---|---|
| | Placebo (N = 11) | T Gel 0.10 g/day (N = 11) | T Gel 0.22 g/day (N = 12) | T Gel 0.44 g/day (N = 12) |
| Baseline (Mean ± SD)[b] | 2.5 ± 1.8 | 2.5 ± 1.8 | 2.1 ± 2.1 | 2.5 ± 1.7 |
| Day 8 | 1.1 | 1.0 | 3.3 | −0.1 |
| Day 15 | 1.6 | 1.2 | 3.6 | −0.4 |
| Day 22 | 1.5 | 1.0 | 3.1 | −0.0 |
| Day 29 | 1.6 | 0.6 | 2.6 | 0.2 |
| Day 36 | 2.1 | 0.6 | 3.1 | 0.0 |
| Day 43 | 2.1 | 0.4 | 3.6 | 0.8 |
| Day 50 | 2.0 | 0.5 | 3.3 | 1.0 |
| Day 57 | 1.5 | 0.5 | 3.9 | 1.0 |
| Day 64 | 1.5 | 0.8 | 3.8 | 1.0 |
| Day 71 | 1.1 | 0.7 | 3.1 | 0.8 |
| Day 78 | 1.5 | 1.5 | 4.6 | 0.5 |
| Day 85/Final[c] | 1.6 | 1.4 | 5.0* | 1.1 |

[a]For Day 8 through Final, means are least square means derived from the ANCOVA model with factors for treatment and baseline 4-week sexual event rate as the covariate.
[b]Unadjusted means and standard deviations. Baseline based on the 8-week Pretreatment Period.
[c]Day subsequent to last completed daily diary record or last dose of randomized study drug, whichever is earlier.
*p-value ≦ 0.05 testing difference in change from baseline from placebo Trough serum samples were obtained prior to dosing on Day 1, Day 29, Day 57, and upon study completion for determination of total, free and bioavailable T, SHBG, and DHT concentrations. Across all treatment groups, median values at Day 1 for Total T (11.0 to 20.0 ng/dL), free T (0.6 to 0.9 pg/mL), bioavailable T (0.8 to 1.1 ng/dL), SHBG (162 to 206 nmol/L), and DHT (2.3 to 6.8 ng/dL) were consistent with a profile for oophorectomized women receiving estrogen therapy.

Figure 2:
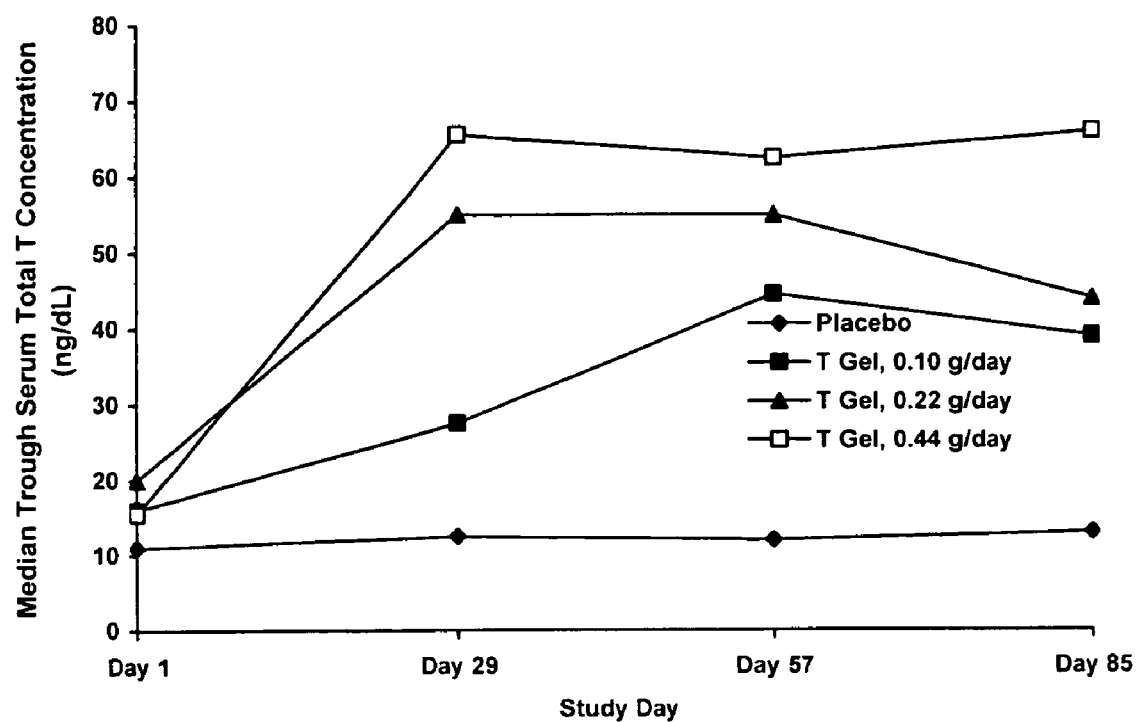
FIG. 2 is a graphic representation of median trough serum total T concentrations after the administration of the present testosterone gel formulation at 1% testosterone in 0.10 g/day, 0.22 g/day, and 0.44 g/day doses, compared to placebo.
Figure 3:
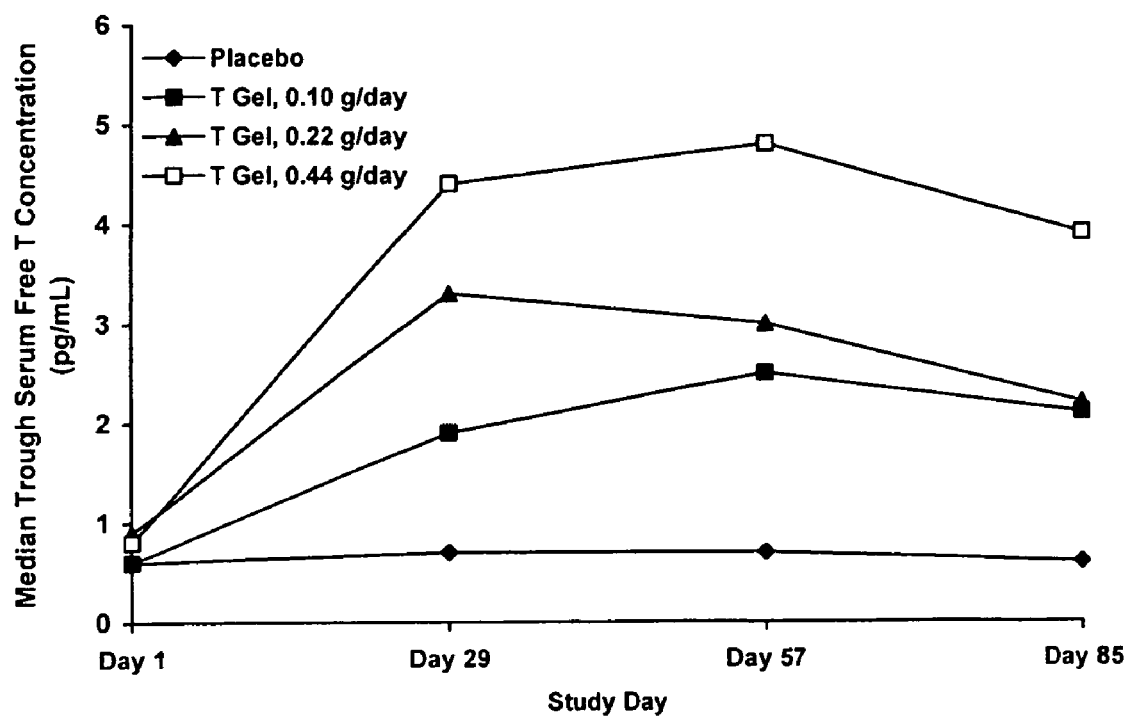
FIG. 3 is a graphic representation of median trough serum free T concentrations after the administration of the present testosterone gel formulation at 1% testosterone in 0.10 g/day, 0.22 g/day, and 0.44 g/day doses, compared to placebo.

After therapy with the present T gel, median total, free, and bioavailable T and DHT concentrations showed separation between treatment groups in accord with T gel dose administration. The median free T values at Day 85 were 2.1 pg/mL, 2.2 pg/mL, and 3.9 pg/mL, respectively, for the T gel 0.10 g/day, 0.22 g/day, and 0.44 g/day dose groups, and were higher than those of the placebo group. For all T gel doses, median serum free T, bioavailable T, and DHT values remained within their respective normal ranges for pre-menopausal women. The median serum concentrations for total T exceeded the normal range (10-55 ng/dL) for the T gel 0.44 g/day dose group. Table 3 shows trough total T, free T, bioavailable T, SHBG, and DHT values during the study. The results for total T and free T are also shown in FIGS. 2-3.

TABLE 3

Trough Total T, Free T, Bioavailable T, SHBG, DHT at Baseline at Days 1, 29, 57, and 85

| Hormone (Normal Range) | Evaluation | Placebo | T Gel 0.10 g/day | T Gel 0.22 g/day | T Gel 0.44 g/day |
|---|---|---|---|---|---|
| Total Testosterone (ng/dL) (10-55 ng/dL) | Day 1 | (N = 11) | (N = 11) | (N = 12) | (N = 12) |
| | Mean ± SD | 11.77 ± 4.10 | 16.65 ± 8.40 | 24.92 ± 20.27 | 14.30 ± 8.54 |
| | Median | 11.0 | 16.0 | 20.0 | 15.5 |
| | Range | 7-19 | 8-36 | 12-88 | 3-35 |
| | Day 29 | (N = 8) | (N = 10) | (N = 11) | (N = 12) |
| | Mean ± SD | 12.34 ± 3.55 | 42.10 ± 32.00 | 52.36 ± 21.41 | 75.08 ± 44.00 |
| | Median | 12.5 | 27.5 | 55.0 | 65.5 |
| | Range | 7-17 | 18-123 | 12-80 | 21-159 |
| | Day 57 | (N = 8) | (N = 10) | (N = 12) | (N = 10) |
| | Mean ± SD | 12.40 ± 4.66 | 64.60 ± 65.86 | 64.33 ± 45.01 | 88.90 ± 57.72 |
| | Median | 12 | 44.5 | 55.0 | 62.5 |
| | Range | 7-22 | 20-242 | 29-192 | 37-230 |
| | Day 85 | (N = 9) | (N = 9) | (N = 11) | (N = 11) |
| | Mean ± SD | 13.52 ± 4.37 | 44.67 ± 22.20 | 47.9 ± 25.78 | 89.27 ± 79.82 |
| | Median | 13.0 | 39.0 | 44.0 | 66.0 |
| | Range | 7-20 | 11-84 | 15-93 | 17-303 |
| Free T (pg/mL) (1.1-6.3 pg/mL) | Day 1 | (N = 11) | (N = 11) | (N = 12) | (N = 12) |
| | Mean ± SD | 0.56 ± 0.23 | 0.85 ± 0.40 | 0.83 ± 0.23 | 0.72 ± 0.29 |
| | Median | 0.6 | 0.6 | 0.9 | 0.8 |
| | Range | 0.2-0.9 | 0.5-1.8 | 0.5-1.2 | 0.2-1.1 |
| | Day 29 | (N = 8) | (N = 10) | (N = 10) | (N = 12) |
| | Mean ± SD | 0.68 ± 0.24 | 2.31 ± 1.62 | 3.19 ± 1.29 | 4.89 ± 2.86 |
| | Median | 0.7 | 1.9 | 3.3 | 4.4 |
| | Range | 0.4-1.0 | 0.6-6.2 | 0.6-5.2 | 1.2-9.5 |
| | Day 57 | (N = 8) | (N = 10) | (N = 12) | (N = 10) |
| | Mean ± SD | 0.68 ± 0.27 | 4.05 ± 4.23 | 3.64 ± 2.90 | 5.68 ± 3.78 |
| | Median | 0.7 | 2.5 | 3.0 | 4.8 |
| | Range | 0.4-1.1 | 1.2-15.0 | 1.1-12.0 | 2.0-14.0 |
| | Day 85 | (N = 9) | (N = 9) | (N = 11) | (N = 10) |
| | Mean ± SD | 0.64 ± 0.35 | 2.19 ± 0.94 | 2.82 ± 2.59 | 5.69 ± 6.65 |
| | Median | 0.6 | 2.1 | 2.2 | 3.9 |
| | Range | 0.2-1.4 | 0.7-3.9 | 0.6-10.0 | 1.7-24.0 |
| Bioavailable T (ng/dL) | Day 1 | (N = 11) | (N = 10) | (N = 12) | (N = 10) |
| | Mean ± SD | 0.85 ± 0.54 | 1.19 ± 0.67 | 1.08 ± 0.35 | 1.00 ± 0.40 |
| | Median | 0.8 | 0.8 | 1.0 | 1.1 |
| | Range | 0.3-2.1 | 0.6-2.6 | 0.6-1.9 | 0.3-1.5 |
| | Day 29 | (N = 8) | (N = 9) | (N = 11) | (N = 12) |
| | Mean ± SD | 1.29 ± 0.97 | 3.67 ± 3.58 | 5.17 ± 2.37 | 8.27 ± 4.76 |
| | Median | 1.1 | 2.5 | 4.5 | 7.7 |
| | Range | 0.5-3.4 | 1.0-13.0 | 0.5-8.4 | 2.6-17.0 |
| | Day 57 | (N = 7) | (N = 9) | (N = 12) | (N = 10) |
| | Mean ± SD | 0.97 ± 0.50 | 6.39 ± 6.03 | 5.12 ± 3.39 | 9.17 ± 4.71 |
| | Median | 0.8 | 5.3 | 4.8 | 8.2 |
| | Range | 0.4-1.6 | 1.8-21.0 | 1.6-14.0 | 3.1-16.0 |
| | Day 85 | (N = 9) | (N = 9) | (N = 11) | (N = 11) |
| | Mean ± SD | 0.86 ± 0.52 | 3.68 ± 2.33 | 4.38 ± 4.77 | 8.19 ± 9.26 |
| | Median | 0.9 | 2.8 | 3.5 | 5.8 |
| | Range | 0.3-2.0 | 0.9-8.9 | 0.9-18.0 | 1.0-33.0 |
| SHBG (nmol/L) (40-120 nmol/L) | Day 1 | (N = 11) | (N = 11) | (N = 12) | (N = 12) |
| | Mean ± SD | 210.0 ± 105.1 | 186.1 ± 102.7 | 209.5 ± 66.8 | 155.5 ± 68.4 |
| | Median | 184 | 162 | 206 | 157 |
| | Range | 100-372 | 45-392 | 125-336 | 45-241 |
| | Day 29 | (N = 8) | (N = 10) | (N = 11) | (N = 12) |
| | Mean ± SD | 221.8 ± 137.1 | 182.2 ± 73.6 | 183.7 ± 80.9 | 164.0 ± 82.0 |
| | Median | 143 | 166 | 167 | 152 |
| | Range | 94-436 | 115-329 | 71-335 | 50-299 |
| | Day 57 | (N = 8) | (N = 10) | (N = 12) | (N = 10) |
| | Mean ± SD | 221.3 ± 131.8 | 166.8 ± 78.4 | 204.9 ± 93.8 | 164.0 ± 81.5 |
| | Median | 186 | 157 | 175 | 132 |
| | Range | 81-378 | 52-351 | 64-377 | 71-303 |
| | Day 85 | (N = 9) | (N = 9) | (N = 11) | (N = 11) |
| | Mean ± SD | 224.0 ± 136.8 | 157.4 ± 59.3 | 188.5 ± 78.8 | 165.4 ± 88.8 |
| | Median | 152 | 151 | 195 | 160 |
| | Range | 80-435 | 51-266 | 65-297 | 51-336 |

TABLE 3-continued

Trough Total T, Free T, Bioavailable T, SHBG, DHT at Baseline at Days 1, 29, 57, and 85

| Hormone (Normal Range) | Evaluation | Placebo | T Gel 0.10 g/day | T Gel 0.22 g/day | T Gel 0.44 g/day |
|---|---|---|---|---|---|
| DHT (ng/dL) (4-22 ng/dL) | Day 1 | (N = 11) | (N = 10) | (N = 12) | (N = 11) |
| | Mean ± SD | 3.86 ± 2.27 | 6.77 ± 4.63 | 5.83 ± 2.36 | 4.12 ± 1.77 |
| | Median | 2.3 | 6.8 | 5.5 | 4.0 |
| | Range | 2.0-8.0 | 2.0-17.0 | 3.1-11.0 | 2.0-7.0 |
| | Day 29 | (N = 8) | (N = 9) | (N = 9) | (N = 12) |
| | Mean ± SD | 3.64 ± 1.78 | 9.14 ± 5.51 | 14.41 ± 4.01 | 14.11 ± 7.06 |
| | Median | 3.1 | 6.6 | 15.0 | 12.5 |
| | Range | 2.0-7.3 | 3.5-18.0 | 9.8-21.0 | 5.6-30.0 |
| | Day 57 | (N = 7) | (N = 9) | (N = 12) | (N = 11) |
| | Mean ± SD | 4.79 ± 1.62 | 14.57 ± 9.53 | 12.61 ± 7.10 | 18.51 ± 13.15 |
| | Median | 4.9 | 11.0 | 10.0 | 12.0 |
| | Range | 2.5-6.5 | 5.8-33.0 | 7.2-32.0 | 7.8-53.0 |
| | Day 85 | (N = 9) | (N = 9) | (N = 11) | (N = 10) |
| | Mean ± SD | 3.99 ± 2.44 | 13.11 ± 13.07 | 11.89 ± 6.85 | 18.64 ± 10.08 |
| | Median | 2.7 | 10.0 | 12.0 | 16.0 |
| | Range | 2.0-7.9 | 3.4-47.0 | 3.6-28.0 | 6.5-41.0 |

[a] Serum hormones measured at an intended visit day were tabulated and used in the analyses only if the measurement was observed within +/−7 days of the intended visit day.

The median serum concentrations of DHEA-S and FSH were within their respective normal ranges at baseline and did not change significantly during the treatment period. Median estradiol and estrone values slightly decreased for the placebo and T gel 0.22 g/day dose groups, and increased for the T gel 0.10 g/day dose group. The median estradiol values for the T gel 0.44 g/day group remained unchanged, but median estrone levels increased. Individual estrogen values were noted to have fluctuations that may have been related to time of blood draw.

Results of the primary analyses of the primary efficacy endpoint indicate that 0.22 g/day is an effective dose of the present testosterone gel for treating hypoactive sexual desire disorder in surgically postmenopausal women. In the T gel 0.22 g/day treatment group, the difference from placebo of 3.4 in mean change from baseline in the 4-week satisfying sexual event rate at Day 85/FinalVisit was both statistically significant (p=0.046) and clinically meaningful (i.e., ≧1.0 event/month). Consistent with the primary endpoint results, the T gel does of 0.22 g/day (2.2 mg T/day) resulted in most improvement in sexual activity and desire frequencies. The T gel 0.22 g/day does also demonstrated the greatest improvement from baseline in sexual desire.

Further, the present T gel compared favorably to placebo in analyses of safety measurements. There were no apparent androgen-related adverse events, such as hirsutism or acne, reported for any T gel-treated subject. Although testosterone is known to increase the risk for hypercoagulability, adverse events related to increased intravascular clotting were not reported in this study, and laboratory coagulation parameters studied (including prothrombin time and aPTT) showed no statistically significant or clinically meaningful mean changes from baseline to final evaluation. Also, no clinically meaningful decreases in prothrombin time or aPTT or increases in platelets were reported. The testosterone treatment with the present T gel also had no significant effects on cholesterol, LDL, HDL or triglycerides. No clinically important effects of the T gel were observed for vital signs, body weight, physical examinations, or skin irritation assessments.

The results of this study demonstrate that daily administration of the present T gel in doses of 1.0-2.2 mg T/day for 12 weeks is a safe and well-tolerated hormone replacement therapy. The treatment increased free and bioavailable T concentrations to within the normal range for pre-menopausal women, and the testosterone dose of 2.2 mg T/day, delivered in 0.22 g/day of T Gel in the study, was determined to be an effective dose in the treatment of hypoactive sexual desire disorder in surgically menopausal women.

Thus, the present testosterone formulation provides advantages over oral, intramuscular, and other transdermal formulations for use in the treatment of HSDD in surgically menopausal women. For example, 1% testosterone in a hydroalcoholic gel that is applied directly to the skin will provide the delivery of testosterone with serum T concentrations that are not subject to first-pass metabolism, while avoiding wide swings in serum concentration and reducing skin reactions as compared to transdermal patch formulations.

What is claimed is:

1. A method for treating hypoactive sexual desire disorder (HSDD) or female sexual dysfunction (FSD) in a female in need thereof, which method comprises the daily and precise administering to a female of between 200 to 240 mg of a formulation that includes about 1% testosterone, an alkanol in an amount between about 5 to 80%, a polyalcohol in an amount between about 1% to 30%, and a permeation enhancer in an amount between about 1 to 30% with the formulation being substantially free of long-chain fatty alcohol, long-chain fatty acid and long-chain fatty ester compounds in order to accurately deliver between 2 to 2.4 mg of testosterone to achieve decreases in or alleviation of at least one of the clinical symptoms of HSDD or FSD in the female and to avoid irritation from such compounds during use of the formulation.

2. The method according to claim 1, wherein the female is a surgically menopausal female, a naturally menopausal female, or a pre-menopausal female.

3. The method according to claim 2, wherein the female has a low free testosterone concentration.

4. The method according to claim 1, wherein the formulation is administered once-per-day from a metered dosage device.

5. The method according to claim 1, wherein the alkanol is provided in combination with water to form a hydroalcoholic mixture, with the alkanol comprising about 5% to 80% by weight of the mixture and the water comprising about 20% to 95% by weight of the mixture, and the hydroalcoholic mixture is present in an amount of about 40 to 98% by weight of the formulation.

6. The method according to claim 1, wherein the alkanol is a $C_2$ to $C_4$ alcohol selected from the group consisting of ethanol, isopropanol, and n-propanol, the polyalcohol is propylene glycol, and the permeation enhancer includes diethylene glycol monomethyl ether, diethylene glycol monoethyl ether, and mixtures thereof.

7. The method according to claim 1, wherein the formulation further comprises at least one of a gelling agent, neutralizing agent, sequestering agent, buffering agent, moisturizing agent, humectant, surfactant, antioxidant, emollient, or buffer.

8. The method according to claim 1, wherein the formulation is provided in the form of a gel, lotion, cream, ointment, emulsion, or suspension.

9. The method according to claim 8, which further comprises accurately controlling the administration of testosterone by dispensing the formulation from a metered dosage device.

10. The method according to claim 9, wherein the metered dosage device dispenses the precise amount of 200 to 240 mg of the formulation to facilitate self administration upon a transdermal or transmucosal surface of the female.

11. A method for treating hypoactive sexual desire disorder (HSDD) or female sexual dysfunction (FSD) in a female by accurately administering testosterone, which comprises administering to the female about 220 mg of a transdermal gel formulation comprising about 1% testosterone, an alkanol in an amount of about 5 to 80% by weight, a polyalcohol in an amount of about 1% to 30% by weight, and a permeation enhancer in an amount of about 1 to 30% by weight of the formulation, wherein the formulation is substantially free of long-chain fatty alcohol, long-chain fatty acid and long-chain fatty ester compounds in order to accurately deliver about 2.2 mg of testosterone from the formulation to achieve decreases in or alleviation of at least one of the clinical symptoms of HSDD or FSD in the female while avoiding irritation from such compounds during administration and use of the formulation.

12. The method of claim 11, wherein the transdermal gel formulation is administered from a metered dosage device, and wherein the alkanol is a $C_2$ to $C_4$ alcohol selected from the group consisting of ethanol, isopropanol, and n-propanol, the polyalcohol is propylene glycol, and the permeation enhancer includes diethylene glycol monomethyl ether, diethylene glycol monoethyl ether, and mixtures thereof, with the alkanol provided in combination with water to form a hydroalcoholic mixture, the alkanol comprising about 5% to 80% by weight of the mixture and the water comprising about 20% to 95% by weight of the mixture, and the hydroalcoholic mixture present in an amount of about 40 to 98% by weight of the formulation.

13. The method of claim 12, wherein the transdermal gel formulation is administered from a metered dosage device in an amount of 220 mg, and wherein the alkanol is ethanol, the polyalcohol is propylene glycol, and the permeation enhancer is diethylene glycol monoethyl ether.

* * * * *

UNITED STATES PATENT AND TRADEMARK OFFICE
CERTIFICATE OF CORRECTION

PATENT NO. : 8,067,399 B2
APPLICATION NO. : 11/441311
DATED : November 29, 2011
INVENTOR(S) : Lehman et al.

It is certified that error appears in the above-identified patent and that said Letters Patent is hereby corrected as shown below:

On The Title Page:
Item (56) References Cited, U.S. PATENT DOCUMENTS
 After "5,188,825 A 2/1993", change "Hes et al." to -- Iles et al. --.

Item (56) References Cited, FOREIGN PATENT DOCUMENTS
 After "EP 0 325 613 B1", change "6/1989" to -- 8/1989 --;
 After "EP 0250125 B1", change "9/1991" to -- 12/1987 --;
 After "EP 0409383 B1", change "4/1994" to -- 1/1991 --;
 After "EP 0491803 B1", change "7/1994" to -- 7/1992 --;
 After "EP 0435200 B1", change "7/1995" to -- 7/1991 --;
 After "EP 0804926 B1", change "10/1999" to -- 11/1997 --;
 After "EP 0655900 B1", change "3/2000" to -- 6/1995 --;
 After "EP 0719538 B1", change "11/2000" to -- 7/1996 --;
 After "EP 0814776 B1", change "7/2001" to -- 1/1998 --;
 After "EP 0643963 B1", change "11/2001" to --3/1995 --;
 After "EP 0868187 B1", change "12/2001" to -- 10/1998 --;
 After "EP 0859793 B1", change "2/2002" to -- 8/1998 --;
 After "EP 1089722 B1", change "5/2002" to -- 4/2001 --;
 After "EP 0802782 B1", change "2/2003" to -- 10/1997 --; and
 After "FR 2518879", change "12/1981" to -- 7/1983 --.

Item (56) References Cited, OTHER PUBLICATIONS
Kotiyan et al. reference, change "173180" to -- 173-180 --;
Lipp reference, change "matrixtype" to -- matrix-type --; and change "13431349" to --1343-1349 --;
Moser et al. reference, change "103112" to -- 103-112 --;
Mura et al. reference, change "36-5372" to -- 365-372 --;
R. Panchagnula et al. reference, change "invitro" to -- in-vitro --;
W.A. Ritschel et al. reference (first occurrence), change "In vitroskin" to -- In vitro skin --;
W.A. Ritschel et al. reference (second occurrence), change "17741777" to -- 1774-1777 --;

Signed and Sealed this
Seventeenth Day of January, 2012

David J. Kappos
*Director of the United States Patent and Trademark Office*

CERTIFICATE OF CORRECTION (continued)
U.S. Pat. No. 8,067,399 B2

Title Page (continued):

J. Rojas reference, after "J. Rojas" insert -- et al. --; and change "perutaneous" to -- percutaneous --;

E. Touitou reference, change "159166" to -- 159-166 --;

M. Yazdanian et al. reference, change "Oflvermectin" to -- of Ivermectin --; and change "309319" to -- 309-319 --;

David W. Osborne et al. reference, after "Literature" insert -- Pharmaceutical Technology, 21(11): 58-66 (1997) --;

"New Drug Application" reference, change "Treatme" to -- Treatment --; and

J. Fang et al. reference, change "Nocotine" to -- Nicotine --; and change "154155" to -- 154-155 --.